United States Patent [19]
Banet et al.

[11] Patent Number: 6,052,185
[45] Date of Patent: Apr. 18, 2000

[54] METHOD AND APPARATUS FOR MEASURING THE CONCENTRATION OF IONS IMPLANTED IN SEMICONDUCTOR MATERIALS

[75] Inventors: Matthew J. Banet, Cambridge, Mass.; John A. Rogers, Castle Rock, Colo.; Martin Fuchs, Uxbridge, Mass.

[73] Assignee: Active Impulse Systems Inc., Mass.

[21] Appl. No.: 08/885,786

[22] Filed: Jun. 30, 1997

[51] Int. Cl.[7] .................................................. G01B 9/02
[52] U.S. Cl. ........................ 356/345; 356/432; 356/359
[58] Field of Search ........................... 356/432, 432 T, 356/318, 359, 360, 345

[56] References Cited

U.S. PATENT DOCUMENTS

| | | |
|---|---|---|
| 4,710,030 | 12/1987 | Tauc et al. . |
| 5,633,711 | 5/1997 | Nelson et al. .......................... 356/432 |
| 5,706,094 | 1/1998 | Maris ..................................... 356/432 |
| 5,734,470 | 3/1998 | Rogers et al. . |

OTHER PUBLICATIONS

Harata, et al., "Laser–Stimulated Scattering Microscope Study of an Ion–Implanted Silicon Surface," Jpn. J. Appl. Phys. vol. 32 (1993) Pt. 1, No. 8, pp. 3633–3638.

*Primary Examiner*—Robert H. Kim

[57] ABSTRACT

A method and apparatus that determines a concentration of ions implanted in a material is described. The method includes the steps of: (1) passing an excitation pulse through a diffracting mask (e.g., a phase or amplitude mask) to generate at least two excitation laser sub-pulses; (2) irradiating a region of the material with a grating pattern, formed by overlapping two excitation laser sub-pulses in time and space to initiate a time-dependent response (e.g., a change in refractive index) in the region; (3) diffracting a probe laser pulse having a duration that is at least long as the time-dependent response off the region to generate a time-dependent signal beam; (4) detecting the time-dependent signal beam to generate a signal waveform; and (5) processing the signal waveform to determine the concentration of ions implanted in the material.

26 Claims, 9 Drawing Sheets

ELECTRONIC

METHOD AND APPARATUS FOR MEASURING THE CONCENTRATION OF IONS IMPLANTED IN SEMICONDUCTOR MATERIALS

BACKGROUND

This invention relates to measuring the concentration of ions implanted in semiconductor materials.

Most microelectronic devices (e.g., a microprocessors) include a series of oxide, metal, and semiconducting films grown or deposited on a semiconducting substrate. The semiconducting substrate is typically a single-crystal silicon wafer, while the semiconducting films are typically an amorphous "polysilicon" material containing small, crystalline regions of silicon. Both silicon wafers and polysilicon films are implanted with high-energy ions during fabrication so that they exhibit a specified electrical conductance. The implanted ions render silicon as being "p" or "n" type. After implantation, both silicon and polysilicon are annealed under high temperatures to heal any lattice damage resulting from the implantation process.

The electrical conductance of silicon and polysilicon is affected by three properties of the implanted ions: (1) atomic composition; (2) implantation energy; and (3) ion concentration or dose. Silicon's electrical conductivity is particularly dependent on the concentration of the implanted ions. For example, silicon wafers are typically implanted with arsenic, argon, phosphorous, oxygen, or boron ions ranging in concentration from $10^{10}$–$10^{16}$ cm$^{-3}$ to improve their semiconducting properties. Polysilicon films are implanted with similar ions at higher concentrations (usually on the order of $10^{20}$ cm$^{-3}$) to function as electrical conductors.

The performance of a completed microelectronic device depends critically on the electrical properties of the silicon wafer and the overlying polysilicon films, and thus the ions implanted in these materials are carefully monitored during fabrication. One property, called electrical sheet resistance, is measured by contacting a sample's surface with an electrical-testing instrument called a 4-point probe. Electrical current flowing from one probe to another depends on the resistance of the material. Resistance, in turn, varies inversely with the concentration of implanted ions.

Ion concentration is also monitored using a non-contact, optical method that excites and detects an electron-hole plasma within the sample. The response of the plasma is influenced by any damage in the semiconductor lattice resulting from the implanted ions. In this measurement, a first laser beam irradiates the semiconducting material and is partially absorbed to generate the electron-hole plasma. The plasma modifies the reflectivity of the sample's surface and can therefore be measured with a second laser beam. The reflected beam is partially reflected by the sample and then analyzed to estimate the properties of the implanted ions.

Although used throughout the microelectronics industry, both 4-point probes and instruments that measure reflectivity suffer disadvantages. 4-point probes necessarily contact the sample, and are therefore destructive. This means that these instruments can only measure "monitor" wafers or regions of "product" wafers that lack functioning devices. Instruments that monitor electron-hole plasmas by measuring reflectivity have limited use and generate signals that are difficult to interpret: they are mostly used to determine whether or not the sample has been ion implanted, rather than the actual concentration of implanted ions.

SUMMARY

The method and apparatus described herein measure the concentration of ions implanted within a semiconducting material with a non-contact, laser-based technique called impulsive stimulated scattering (ISS). ISS initiates and measures two different types of responses, both of which depend on the concentration of implanted ions: (1) time-dependent changes in the sample's optical properties (i.e., complex refractive index), referred to herein as an "electronic" response; and (2) time-dependent acoustic phonons, referred to herein as an "acoustic" response. Whether or not one or both of the responses is measured depends on the sample and the properties of the lasers used during ISS. For example, ion-implanted samples containing silicon typically exhibit an electronic response following absorption of radiation during ISS. In this case, optical absorption generates a time-dependent change in the sample's refractive index, resulting in a response that rapidly increases in amplitude and then decays away with an exponential time constant. Both the decay constant and amplitude of the response depend on the concentration of the implanted ions. If the optical wavelength used in ISS is very strongly absorbed (e.g., within a few hundred nanometers of the sample s surface), an acoustic response results that includes coherent acoustic phonons propagating through the lattice of the ion-implanted semiconductor. In this case, the response exhibits oscillations at a frequency that depends on the concentration of the implanted ions.

ISS generates a signal waveform characterized by one or both of the electronic and acoustic responses. The properties of the signal waveform are then analyzed to determine the concentration of the implanted ions. This concentration is then analyzed and used to control fabrication processes used to make microelectronic devices.

In one aspect, the invention provides a method that determines a concentration of ions implanted in a material. The method includes the steps of: (1) passing an excitation pulse through a diffracting mask (e.g., a phase mask) to generate at least two excitation laser sub-pulses; (2) irradiating a region of the material with a grating pattern, formed by overlapping two excitation laser sub-pulses in time and space to initiate a time-dependent response (e.g., a change in refractive index) in the region; (3) diffracting a probe laser pulse having a duration that is at least long as the time-dependent response off the region to generate a time-dependent signal beam; (4) detecting the time-dependent signal beam to generate a signal waveform; and (5) processing the signal waveform to determine the concentration of ions implanted in the material.

In embodiments, the processing step includes the step of comparing the signal waveform to a mathematical function, and then determining an amplitude of the mathematical function to determine the amplitude of the signal waveform at a point in time. The mathematical function, for example, could be a function used to fit the signal waveform. In some cases, the mathematical function includes an exponential function, e.g., $S_0(t_0) [Ae^{-(t+t0)/\tau}]$ or a derivative thereof, where A is the amplitude, $\tau$ is a decay constant, t is time, and $S_0$ is a unit step function starting at $t=t_0$. Once the amplitude is determined, the processing step can further include the step of comparing the amplitude to valves in a database that correlates amplitudes of previously measured signal waveforms to concentrations of ions implanted in representative materials. This comparison determines the concentration of ions implanted in the material. Alternatively, the analyzing step includes analyzing the amplitude with a mathematical algorithm, such as a first-principles calculation, to determine the concentration of ions implanted in the material. For example, the first-principles calculation could include modeling the kinetics of the response of the sample to determine the ion implant concentration. In other embodiments, the processing step includes digitizing the signal waveform to generate a data set, and then determining the amplitude of the signal waveform at a point in time by selecting a value from the data set. In still other embodiments, the processing step can include the steps of plotting the signal waveform as a function of time, calculating the area underneath the plot, and then comparing this value to a valve in a database determine the concentration of implanted ions.

In typical applications, the sample is a silicon-containing material, e.g., a polysilicon film or a silicon wafer. Other materials that can be measured include films and wafers containing gallium arsenide, aluminum gallium arsenide, germanium, and derivatives and analogs thereof. Other samples that can be measured include ceramic materials, metals, and any other material that can be implanted with ions. The ions that can be implanted in these materials include ions of arsenic, argon, boron, oxygen and phosphorous atoms.

In another aspect, the invention provides a method for determining a concentration of ions implanted in a silicon or polysilicon sample. The method includes the steps of: 1) generating at least two excitation laser sub-pulses; 2) irradiating a region of the material with a grating pattern, formed by overlapping at least two excitation laser sub-pulses, to initiate a time-dependent, decaying, non-oscillatory response in the region; 3) diffracting a probe laser pulse, having a duration that is at least long as the time-dependent response, off the region to generate a time-dependent signal beam; 4) detecting the time-dependent signal beam to generate a signal waveform; and 5) processing the signal waveform to determine the concentration of ions implanted in the silicon or polysilicon sample.

The method described above is carried out with an apparatus that includes: (1) an excitation laser for generating an excitation laser pulse; (2) a beam-delivery system including a diffracting mask for separating the excitation laser pulse into at least two sub-pulses and then overlapping the sub-pulses in a region of the material to form a grating pattern; (3) a probe laser that generates a probe laser pulse that exceeds the duration of the time-dependent response and is oriented to diffract off the region to generate a time-dependent signal beam; (4) a photodetector for detecting the time-dependent signal beam to generate a signal waveform; and (5) a processor (e.g., a computer) for processing the signal waveform as described above to determine the concentration of ions implanted in the material.

The diffracting mask, for example, can be a phase or amplitude mask containing a pattern of spatially varying opaque bars or transparent grooves.

The above-described method and apparatus have many advantages when compared to conventional techniques for measuring the concentration of implanted ions. In general, ISS is an accurate, quantitative method for determining the concentration of ions implanted in both semiconductor substrates and thin films. The method is all-optical, non-contact, and non-destructive, and can therefore measure semiconductor materials used in actual devices (i.e., production samples), rather than monitor samples. This information can then be used by manufacturers to improve both the yield and performance characteristics of microelectronic devices containing these materials.

The apparatus for making ISS measurements is compact, easily automated, and collects signal waveforms having very high signal-to-noise ratios. In particular, the diffracting masks, and particularly the phase masks, simplify the alignment of the excitation and probe laser beams and allow the grating pattern to be changed in a rapid, facile manner. This arrangement forms a grating pattern that maximizes the signal waveform amplitude for a particular material to be rapidly and easily selected. The phase mask also eliminates the need for additional beam-delivery optics, such as additional lenses and beamsplitters, that are normally required for ISS measurements. Likewise, use of a probe pulse having a duration that exceeds the time-dependent response allows the user to collect (and then average) entire signal waveforms with a single laser shot. This significantly reduces the time required to measure high-quality data and further eliminates the need for additional data-collection optics, such as a mechanical delay line for delaying a probe pulse relative to the excitation pulses.

Measurements with the above-mentioned apparatus are made rapidly (typically requiring only a few seconds) and with high spatial resolution (typically using a probe beam having a spot size of about 25 microns or less). Thus, small features of the sample, such as a small-scale test site of a microelectronic device or an area near a wafer's edge, can be easily measured. Moreover, the above-mentioned apparatus can be incorporated into a facile, compact, easy-to-use instrument that can be employed in a microelectronic-device fabrication facility. The instrument, for example, can be attached to a production tool and used to make in situ measurements of an ion-implantation process.

Still other advantages will be apparent from the following detailed description, and from the claims.

DETAILED DESCRIPTION

Method for Measuring Ion Implantation Concentration with ISS

Figure 1:
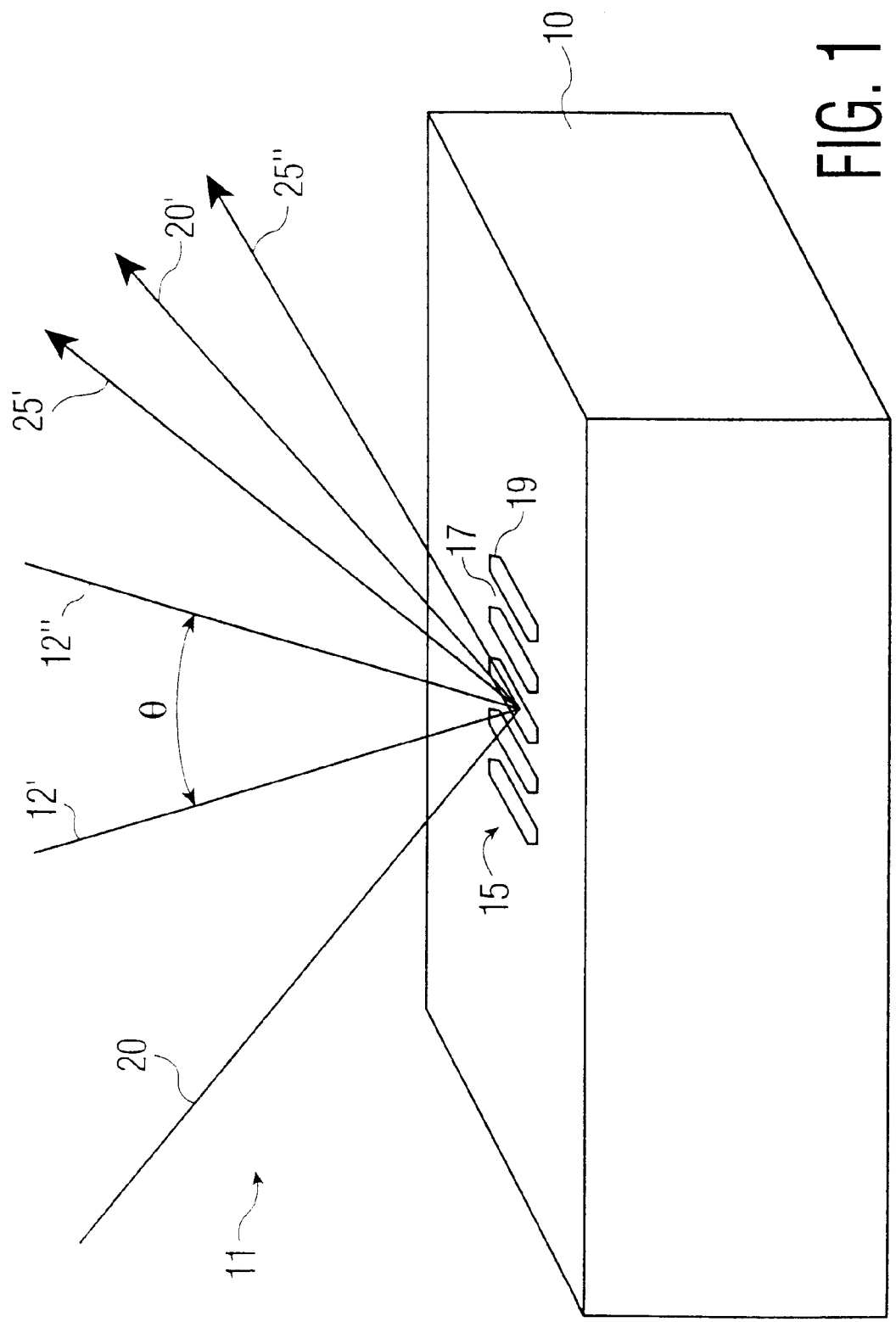
FIG. 1 is a schematic drawing of the ISS method.

Referring to FIG. 1, the concentration of ions implanted in a sample 10 (e.g., silicon) is measured with an optical, laser-based technique 11 called impulsive stimulated scattering (ISS). Applicants have described the use of a related laser-based technique, called ISTS, to measure other material properties in MEASUREMENT OF MATERIAL PROPERTIES WITH OPTICALLY INDUCED PHONONS (U.S. Pat. No. 5,633,711); SIMPLIFIED DEVICE AND METHOD FOR TIME-RESOLVED OPTICAL MEASUREMENTS (U.S. Ser. No. 08/377,310, filed Jan. 24, 1995); METHOD AND DEVICE FOR MEASURING FILM THICKNESS (U.S. Ser. No. 08/783,046, filed Jul. 15, 1996); and IMPROVED METHOD AND APPARATUS FOR MEASURING MATERIAL PROPERTIES USING TRANSIENT GRATING SPECTROSCOPY (U.S. Ser. No. 08/885,555, filed concurrently herewith). These references are therefore incorporated herein by reference.

In ISS, a pair of optical pulses 12', 12" from an excitation laser (not shown in the figure) separated by an angle θ are overlapped in time and space in a region 15 on the sample's surface. The optical pulses 12', 12" typically have a duration of between 0.3 and 0.7 nanoseconds (i.e., 0.3 and $0.7 \times 10^{-9}$ seconds), an energy of about 5 microjoules/pulse, and a wavelength that is absorbed by the sample; for silicon, the wavelength is in either the visible or infrared spectral region. Interference between the overlapped pulses 12', 12" forms a spatially varying "grating" pattern 15 containing alternating "light" (constructive interference) 17 and "dark" (destructive interference) 19 regions. Radiation is absorbed by the sample 10 in the light regions 17, but not in the dark regions 19 of the grating pattern. The absorbed radiation initiates both time-dependent acoustic and electronic responses having properties that depend on the concentration of the ions implanted in the sample 10. These responses are measured in their entirety by irradiating a region near the grating pattern 15 with a probe pulse 20. The probe pulse 20 has a duration (typically several hundred microseconds) that is longer than both the electronic and acoustic responses and a peak power of several hundred milliwatts; the wavelength of the probe pulse is typically in either the visible or infrared spectral regions. The probe pulse is partially reflected to form a reflected beam 20', and partially diffracted to form a pair of signal beams 25', 25" that are the +1 and −1 diffracted orders. One or both of the signal beams 25', 25" is detected with a photodetector (not shown in the figure) to generate a signal waveform. The signal waveform is then analyzed to determine the concentration of the implanted ions.

Whether or not the sample's response is electronic, acoustic, or both depends in part on how strongly the radiation in the light regions of the grating pattern 15 is absorbed by the sample. For example, silicon has a band gap near 900 nm: radiation having an energy above the band gap (e.g., visible radiation) is therefore absorbed over a shorter pathlength than radiation having an energy below the band gap (e.g., radiation at 1 micron). An electronic response typically results when the excitation radiation has an energy that is above or slightly below the band gap. Without being bound to any theory, it appears that in this case ISS generates excited-state charge carriers (e.g., electron-hole pairs) in the light regions, but not the dark regions of the grating pattern. The density of charge carriers depends on the concentration of ions implanted in the sample. Once generated, the charge carriers have a finite lifetime and recombine with a time constant on the order of several nanoseconds. During this period the sample's refractive index in the light regions is temporarily changed relative to the refractive index in the dark regions. This results in a spatially periodic variation in refractive index (i.e., a phase grating) that diffracts the probe radiation during the lifetime of the charge carriers. An increase in the concentration of implanted ions will increase the number of excited charge carriers and, consequently, the difference in refractive index between the light and dark regions of the grating pattern. This, in turn, increases the intensity of the diffracted probe beam and the amplitude of the ISS signal waveform.

To verify this explanation, data were collected at a number of different grating patterns, each having a different spatial frequency. The decay time constants describing these data showed no dependence on the grating pattern, indicating that the signal waveform was not due to a diffusive process (e.g., thermal diffusion).

An acoustic response results from radiation-induced heating generated by ISTS. This technique has been described in detail in MEASUREMENT OF MATERIAL PROPERTIES WITH OPTICALLY INDUCED PHONONS (U.S. Pat. No. 5,633,711); SIMPLIFIED DEVICE AND METHOD FOR TIME-RESOLVED OPTICAL MEASUREMENTS (U.S. Ser. No. 08/377,310, filed Jan. 24, 1995); and METHOD AND DEVICE FOR MEASURING FILM THICKNESS (U.S. Ser. No. 08/783,046, filed Jul. 15, 1996). Briefly, during ISTS excitation radiation is absorbed by the sample in the light regions of the grating pattern during the short duration of the excitation pulse. These regions then undergo a rapid thermal expansion to launch counter-propagating acoustic waves having a wavelength and orientation that match the spatial properties of the grating pattern. Acoustic waves oscillate at a frequency that is determined by their wavelength and the acoustic properties of the sample (i.e., the density and longitudinal and transverse sound velocities). The concentration of implanted ions increases the stiffness of the host lattice and therefore affects these properties. During the measurement, the acoustic frequency of the ISTS-excited acoustic wave is thus measured to determine the concentration of the implanted ions. In this case, the acoustic response is optimized when the excitation radiation is strongly absorbed over a relatively short (e.g., a few hundred nanometers) pathlength in the sample. For silicon and polysilicon, this means that the excitation radiation typically has a wavelength in the visible or ultraviolet portion of the spectrum.

Figure 2:
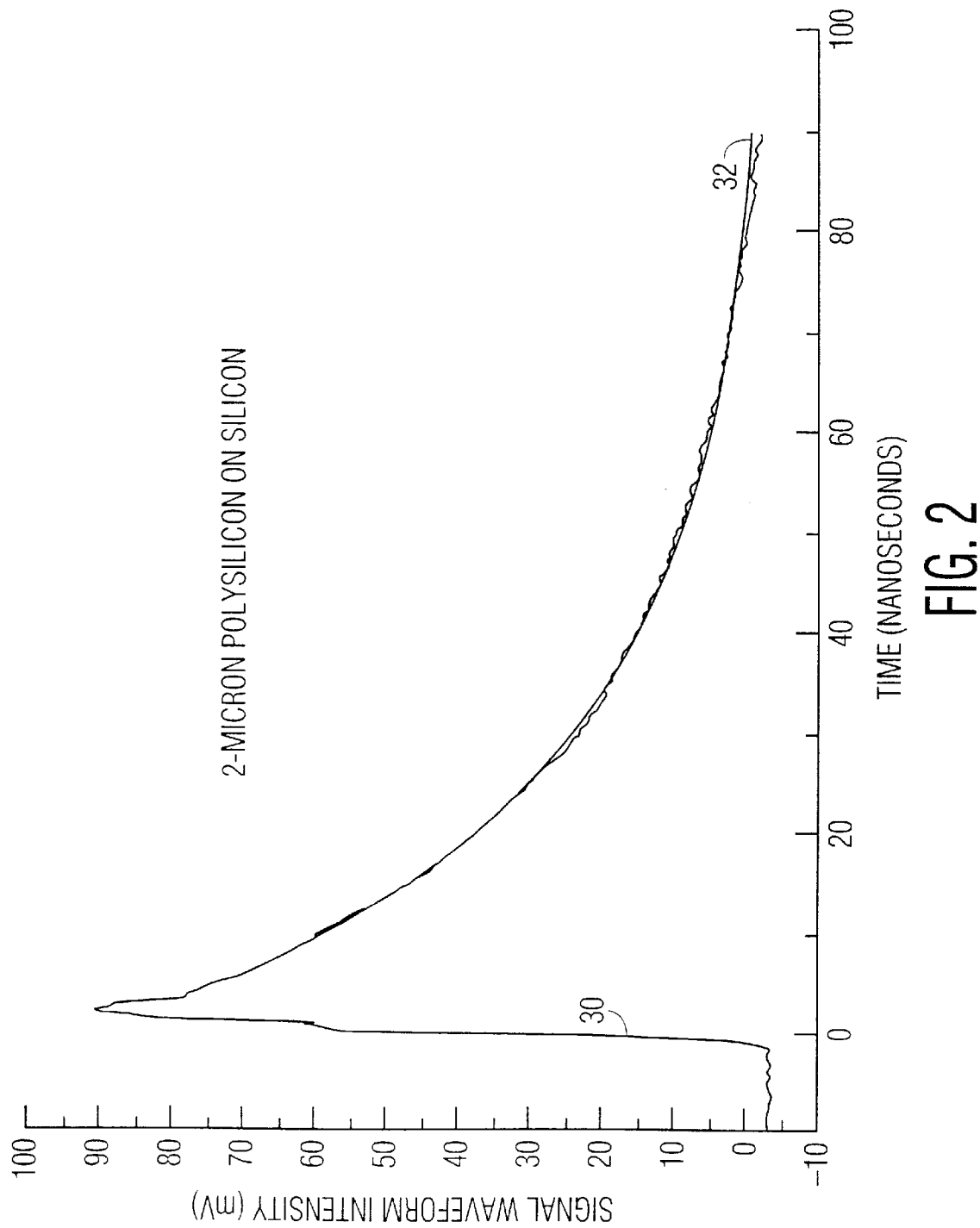
FIG. 2 is a graph of a time-dependent signal waveform characterized by an electronic response measured from a 2-micron, ion-implanted polysilicon film deposited on a silicon wafer.

FIGS. 2 and 5 show signal waveforms (30 in FIG. 2; 31 and 32 in FIG. 5) characterized, respectively, by electronic (FIG. 2) and acoustic (FIG. 5) responses. The data in FIG. 2 were measured from a 2-micron polysilicon film deposited on a 100-mm silicon wafer. The film was implanted with an average concentration of approximately $10^{20}$ $cm^{-3}$ arsenic ions and then annealed to heal any damage to the polysilicon. Measurements were made with excitation pulses having a wavelength of 1.064 microns, a duration of about 0.5 nanoseconds, and an energy of about 3.5 microjoules/pulse from a Nd:YAG laser. The excitation pulses were generated by passing a single excitation laser beam through a phase mask. The probe laser had a wavelength of 860 nm, a pulse duration of 200 microseconds, and a peak power of 200 mW. As is clear from the data, the signal waveform has a well-defined decaying component but no oscillating component, indicating an electronic response. The waveform decays from a value of about 40 mV at 20 nanoseconds to a value of about 10 mV at 60 nanoseconds. This decay is accurately fit with a single-exponential fitting function 32 having the form $S_0(t_0)[Ae^{-(t+t0)/\tau}]$, where A is the amplitude of the fit (in units of mV) and $\tau$ is the decay constant (in units of nanoseconds). $S_0$ is a unit step function starting at $t=t_0$. The fit to the signal waveform 30 was generated with a conventional fitting algorithm that iteratively adjusts the parameters of the fitting function 32 (i.e., $S_0$, A, $t_0$, and $\tau$ described above) until this function best matches the signal waveform. The amplitude value A is then determined from the fitting function and further analyzed to determine the ion implantation concentration.

Figure 3A:
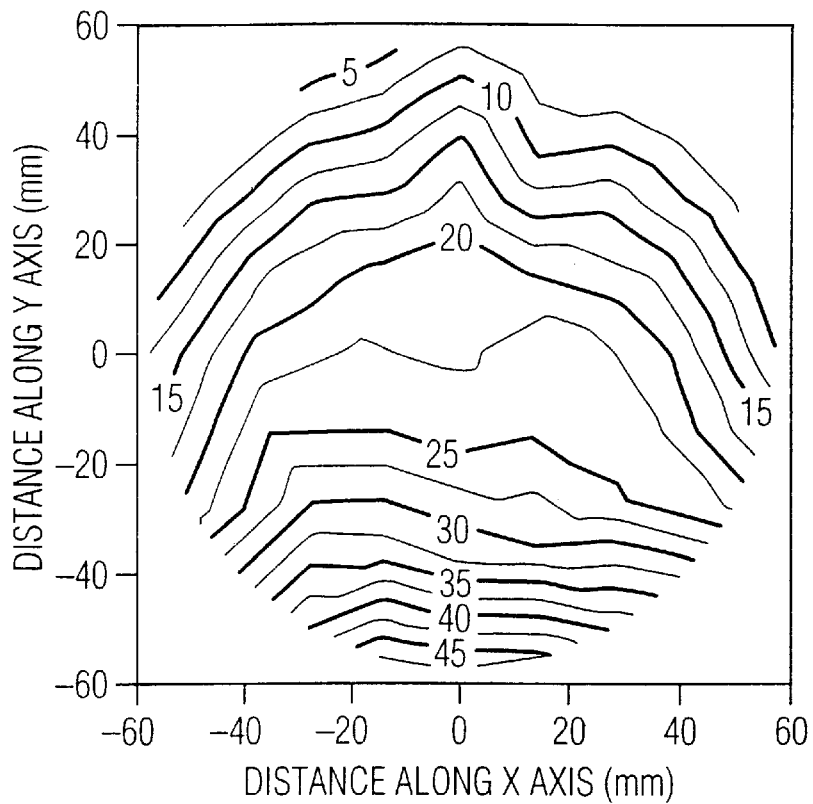
FIGS. 3A–3B are graphs of two-dimensional, 49-point contour maps of, respectively, the amplitude (in mV) of a signal waveform measured with ISS and sheet resistance (in normalized units) measured with a 4-point probe from a 2-micron polysilicon film deposited on a 100-mm diameter silicon wafer.

FIG. 3A shows how the concentration of implanted ions varies across the polysilicon film. Data for this figure were measured by determining the amplitude of the signal waveform at 49 separate points distributed in a standard, radial pattern. Data were acquired using the instrument described above. The points are contained in three equally spaced concentric rings, with the first point in the center of the wafer, points 2-8 in the first ring, points 9-25 in the second ring, and points 26-49 in the third ring. Amplitudes (A) measured from signal waveforms at each point on the sample are plotted in a contour format using a linear interpolation algorithm. The time constant ($\tau$) was roughly the same for each signal waveform.

Figure 3B:
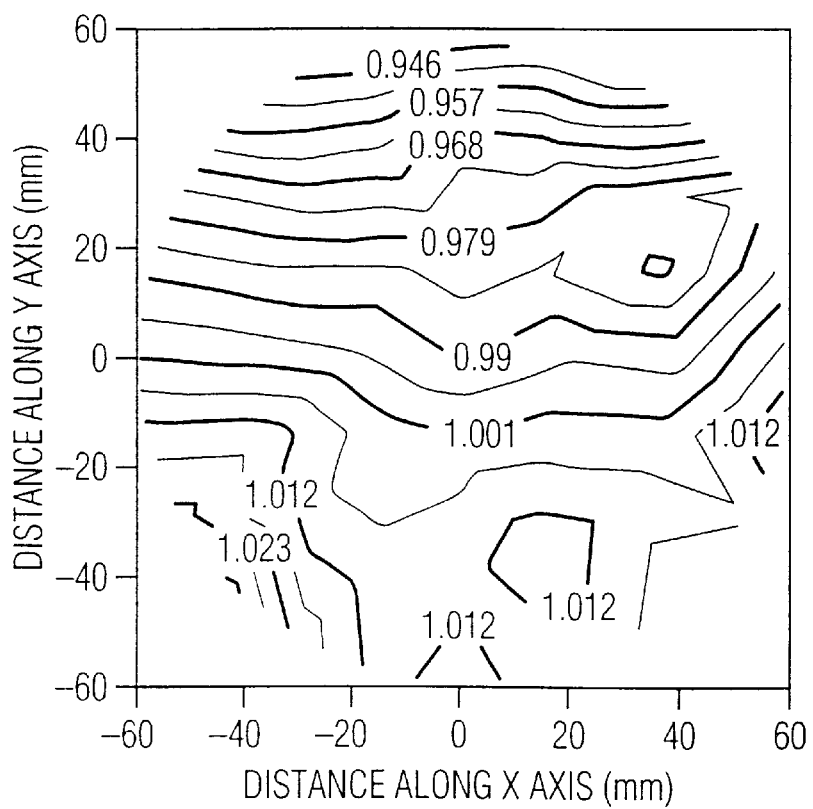
Figure 3C:
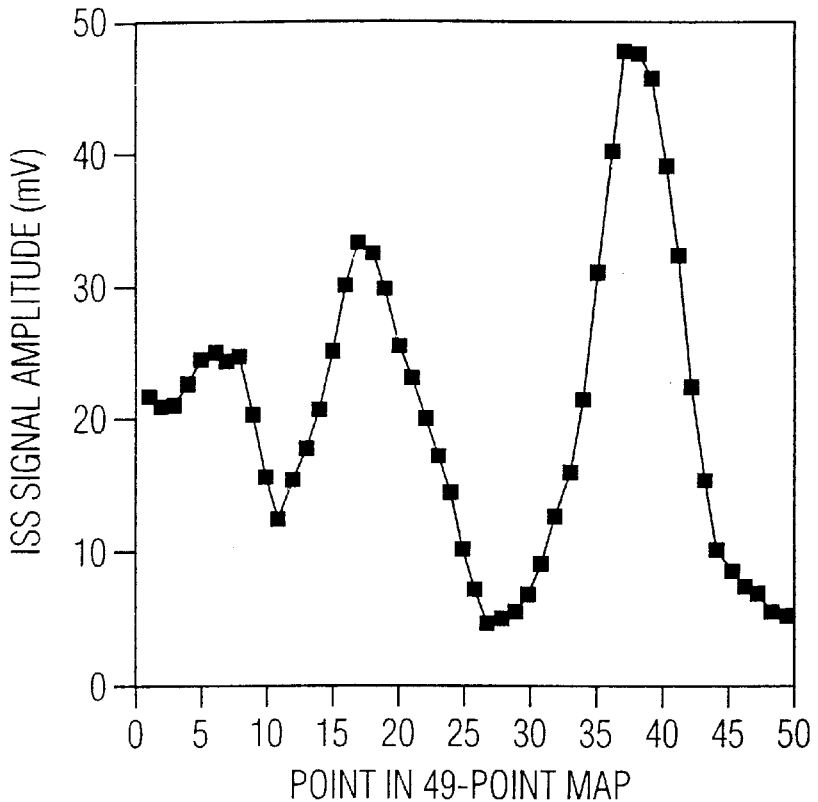
FIGS. 3C–3D are graphs of, respectively, the amplitude (in mV), and sheet resistance (in normalized units), values from FIGS. 3A–3B plotted for each point in the 49-point map.

As shown in FIG. 3A, the amplitude of the signal waveform varies smoothly and systematically across the surface of the polysilicon sample; the variations are both large and highly repeatable. The signal waveform amplitude is maximized near the bottom, central portion of the polysilicon film (x=0 mm, y=-50 mm) and decreases systematically from the bottom portion to the top portion of the water FIG. 3C shows the same data in a different format, with the amplitudes of the signal waveforms measured for FIG. 3A plotted as a function of the points in the 49-point contour map. Each point is indicated by a square in the figure. These data show the smooth, systematic variation of the data for the different points in the map, with the regions having relatively high ion implant concentrations yielding amplitudes in the range of 40-50 mV, and the regions of relatively low ion implant concentrations yielding amplitudes in the range of 5-15 mV. The regions of relatively high and low amplitudes correspond to concentrations of approximately $10^{21}$ cm$^{-3}$ and $10^{19}$ cm$^{-3}$, respectively.

Figure 3D:
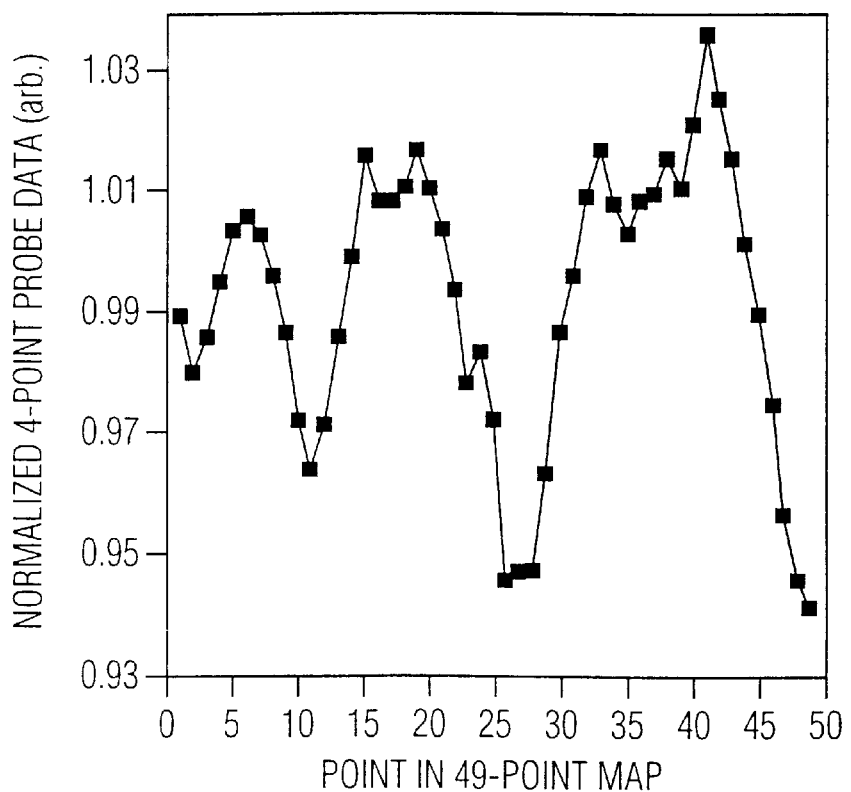

The same polysilicon film was measured with a 4-point probe to verify that the amplitude of the ISS waveform is, in fact, representative of the concentration of ions implanted in the polysilicon. As described above, the 4-point probe measures electrical sheet resistance, a well-known property that is inversely related to the concentration of implanted ions. FIG. 3B shows a 49-point contour map of the normalized, inverse sheet resistance measured in a concentric-ring pattern similar to that used in FIG. 3A. Similarly, FIG. 3D shows the data plotted in a point-by-point format like FIG. 3C. Comparing these figures indicates that the ISS and 4-point probe data correlate quite well, both showing a "distribution of implanted ions that is maximized near the bottom, center portion of the polysilicon sample and decreases towards the top, central portion of the sample. Comparison between FIGS. 3C and 3D show that the ISS data have, in general, a higher signal-to-noise ratio than the 4-point probe data. Discrepancies between the contours of FIGS. 3A and 3B exist because the two experiments measure slightly different points on the polysilicon sample and are susceptible to different types of factors (e.g., impurities, surface quality, substrate effects) that may result in error.

Data similar to that shown in FIGS. 2 and 3A-3F were also measured from similar 2-micron polysilicon films that were not annealed. As before, the data were characterized by an electronic response that was highly repeatable and could be fit with a single-exponential function. Like that shown above for the annealed film, the data for the un-annealed film varied smoothly and systematically across the wafer and depended on the concentration of implanted ions.

Figure 4A:
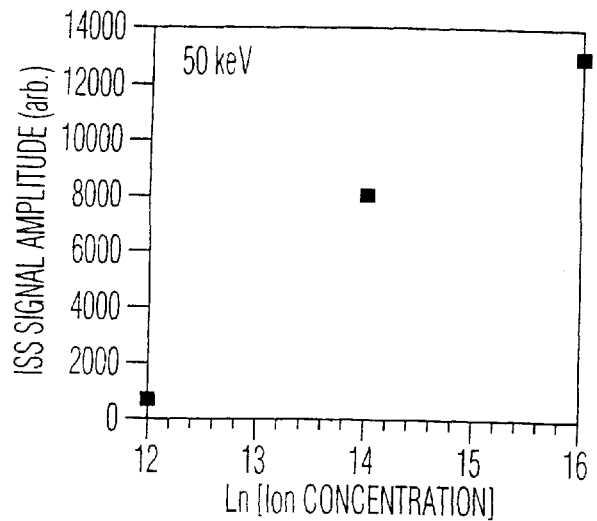
FIGS. 4A–4C are graphs of the signal waveform amplitude (in mV) vs. the log of ion implant concentration measured from a set of ion-implanted silicon wafers implanted with, respectively, ions implanted at 50, 80, and 110 KeV.
Figure 4B:
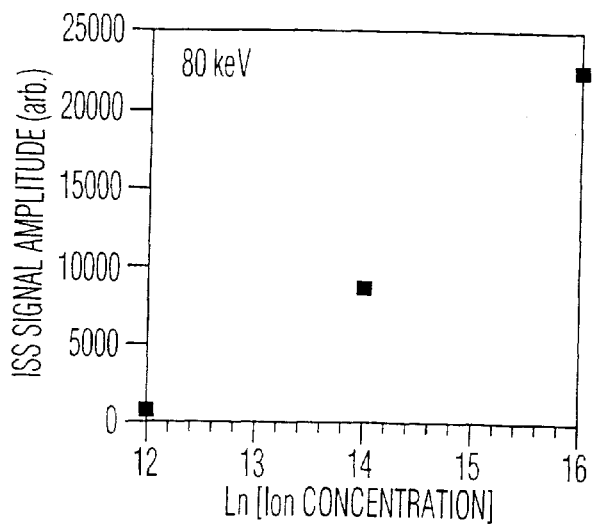
Figure 4C:
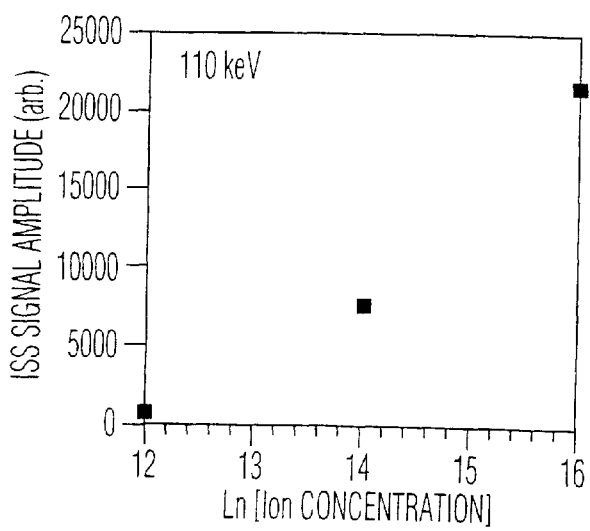

In a separate set of experiments, electronic responses were measured from a set of 100-mm diameter silicon wafers implanted with argon ions at different enregics. FIGS. 4A-4C show the signal waveform amplitude measured plotted as a function of ion implant concentration for three different silicon wafers having concentrations ranging from $10^{12}-10^{16}$ cm$^{-3}$. The implant energy for each of these samples ranged from 50-110 keV. The data were measured from a center point of each wafer using ISS and the same instrument used to measure the polysilicon samples.

Signal waveforms measured from each sample exhibited an electronic response similar to that measured from the polysilicon samples. In this case, the signal amplitude was determined by calculating the area underneath the signal waveform. FIGS. 4A-4C each show that the signal waveform amplitude increases systematically with the log of the concentration of implanted ions for each of the implantation energies. The dependence of the amplitude on the log of implantation concentration is basically linear to each implantation energy.

Data like that shown in FIGS. 4A-4C can be stored in a database and later accessed to determine quantitatively the concentration of ions implanted in a sample during an actual fabrication process. In a particular example, data (i.e., signal waveform amplitude vs. ion implant concentration) from a set of test samples having a systematically varying concentration of implanted ions are generated and verified with electrical testing instruments, such as a 4-point probe. These data are then stored in a database on a computer. When ISS measurements are made on actual product samples during fabrication the amplitude of the signal waveforms are determined by fitting the data as described above. The resulting amplitude is then compared to values in the database to determine quantitatively the concentration of implanted ions.

Figure 5A:
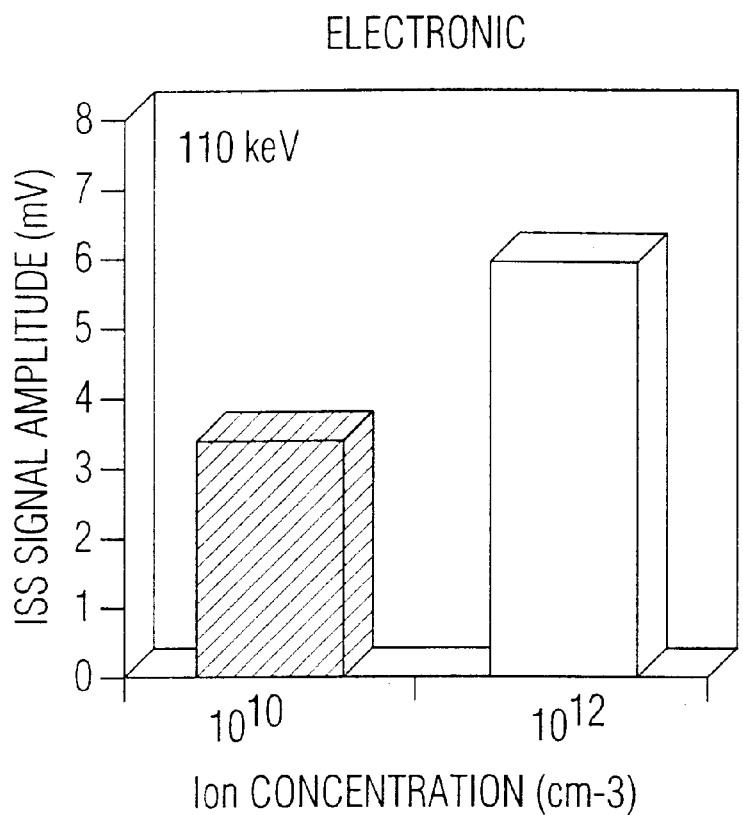
FIGS. 5A and 5B are graphs of the signal waveform amplitude (in mv) vs. log of ion implant concentration measured from silicon wafers implanted, respectively, with ions at 110 and 160 KeV.
Figure 5B:
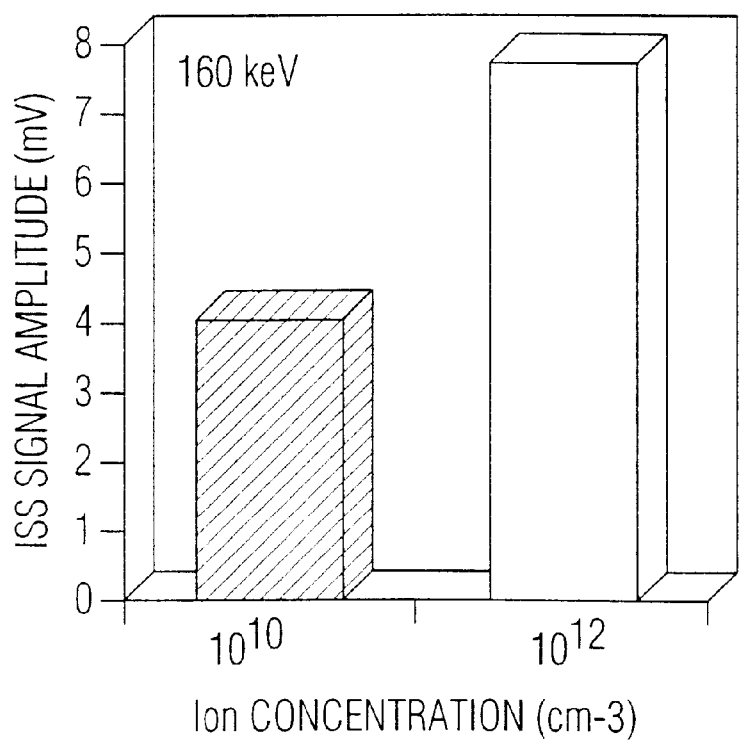

FIGS. 5A and 5B show how the ISS signal amplitude varies with ion implantation concentration for relatively high-energy, low-concentration implantation processes (i.e., less than $10^{12}$ ions/cm$^3$ and implantation engeries at 110 and 160 eV). The data shown in these figures are consistent with that shown in FIGS. 4a-4C, and indicate an increase in ISS signal amplitude with increasing concentration.

ISS can also measure an acoustic response, like that shown in FIG. 2B, that correlates to the concentration of implanted ions. FIG. 6 shows two signal waveforms 31, 32 measured from different 8-inch silicon wafers implanted with arsenic ions at concentrations of, respectively, $10^{14}$ and $5\times10^{14}$ cm$^{-3}$. Both signal waveforms exhibit an oscillating, acoustic response. The signal waveforms shown in these figures were measured using ISS and an excitation pulse having a wavelength of 532 nm, a pulse duration of 0.2 nanoseconds, and an energy of about 5 microjoules/pulse. The probe pulse had a wavelength of 514 nm, a pulse duration of 200 microseconds, and a peak power of 100 mW. Inspection of FIG. 5 indicates the signal waveform 32 measured from the sample implanted with $5\times10^{14}$ cm$^{-3}$ includes an electronic response characterized by an exponential decay during the first 5 nanoseconds, and an acoustic response that oscillates and decays over a time period of about 70 nanoseconds. The frequency of oscillation for the acoustic responses measured from this sample is approximately 550.5 MHz. The signal waveform 31 measured from the sample implanted with $10^{16}$ ions includes a comparable acoustic response but a relatively weak electronic response. The frequency of oscillation for the acoustic responses measured from this sample is approximately 550 MHz. Larger differences in frequency are expected when the excitation pattern is adjusted to excite a higher acoustic frequency.

Figure 5C:
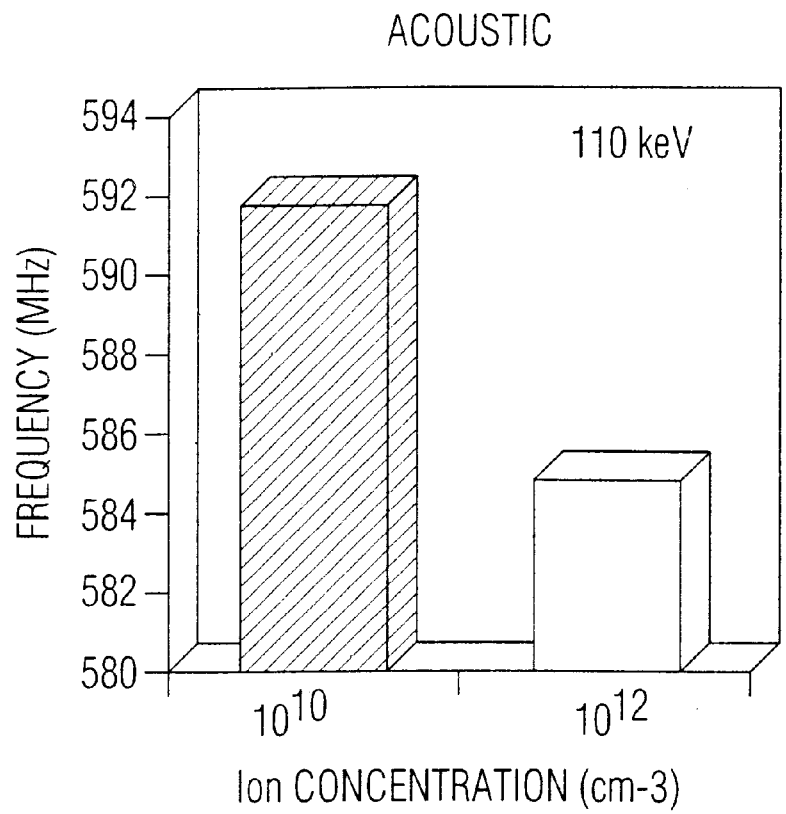
FIGS. 5C and 5D are graphs of the acoustic frequency (in MHz) vs. log ion implant concentration measured from silicon wafers implanted, respectively, with 110 and 160 KeV.
Figure 5D:
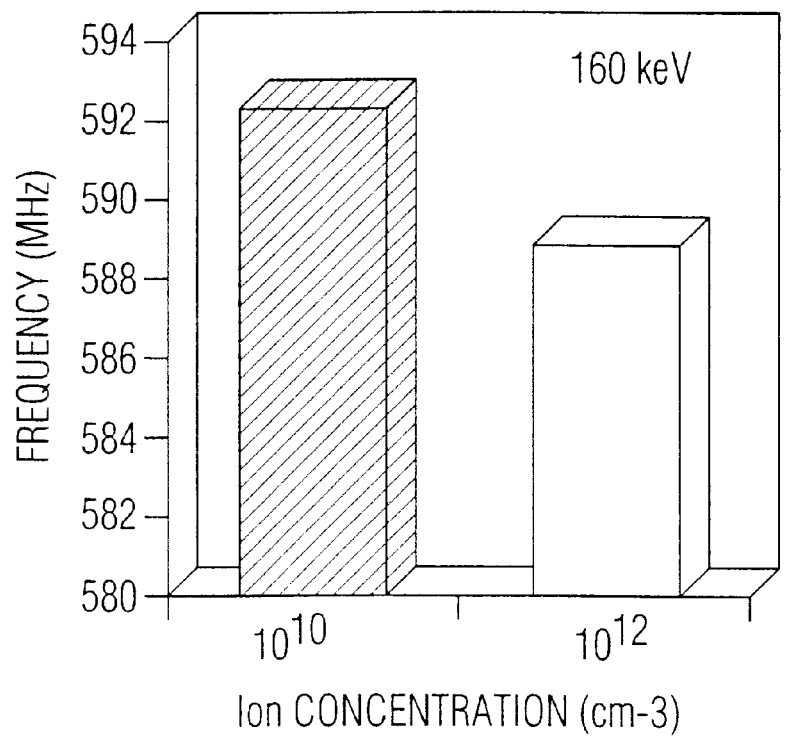
Figure 6:
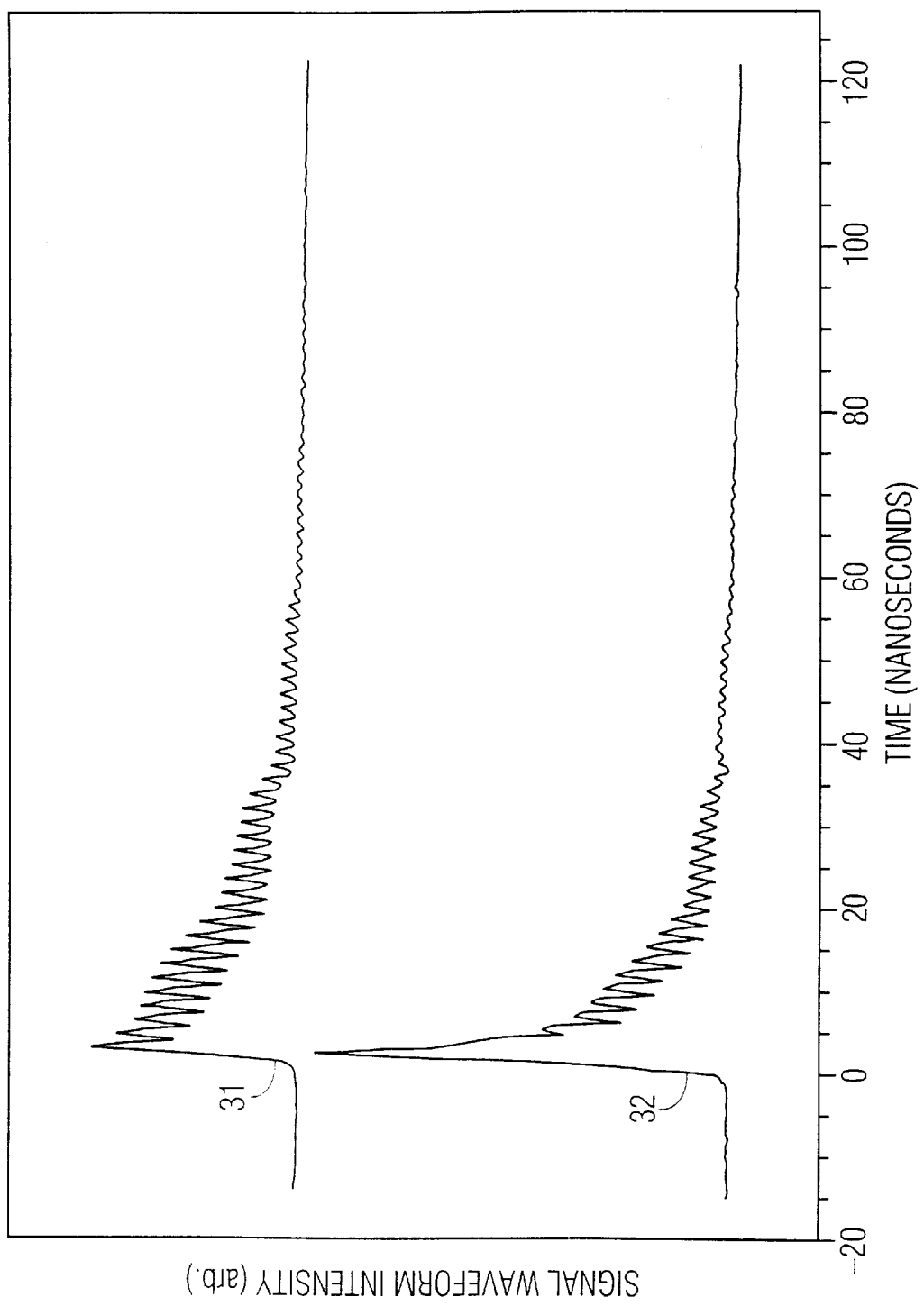
FIG. 6 is a graph of time-dependent signal waveforms characterized by an acoustic response measured from silicon wafers implanted with, respectively, $10^{16}$ (bottom) and $5 \times 10^{16}$ (top) arsenic ions $cm^{-3}$.

FIGS. 5C and 5D show consistent results measured from silicon wafer implanted with ions at high energies and low concentrations. In this case, the acoustic frequency was measured to be about 592 MHz for both the 100 KeV and 160 KeV samples implanted at $10^{10}$ ions/cm$^{-3}$. This acoustic frequency decreased to about 584 MHz for the sample implanted with ions at 110 KeV and $10^{12}$ cm$^3$, and to about 588 MHz for ions at 160 KeV and $10^{12}$ cm$^{-3}$.

As described above, the dependencies of both the electronic and acoustic responses on ion concentration can be calibrated using a well-defined set of test samples to generate a database. Once the relationship between frequency and ion implant concentration is determined, measurements from actual product wafers can be compared to the database to determine the ion implantation concentration.

Apparatus for Determining Ion Implant Properties Using ISS

Figure 7:
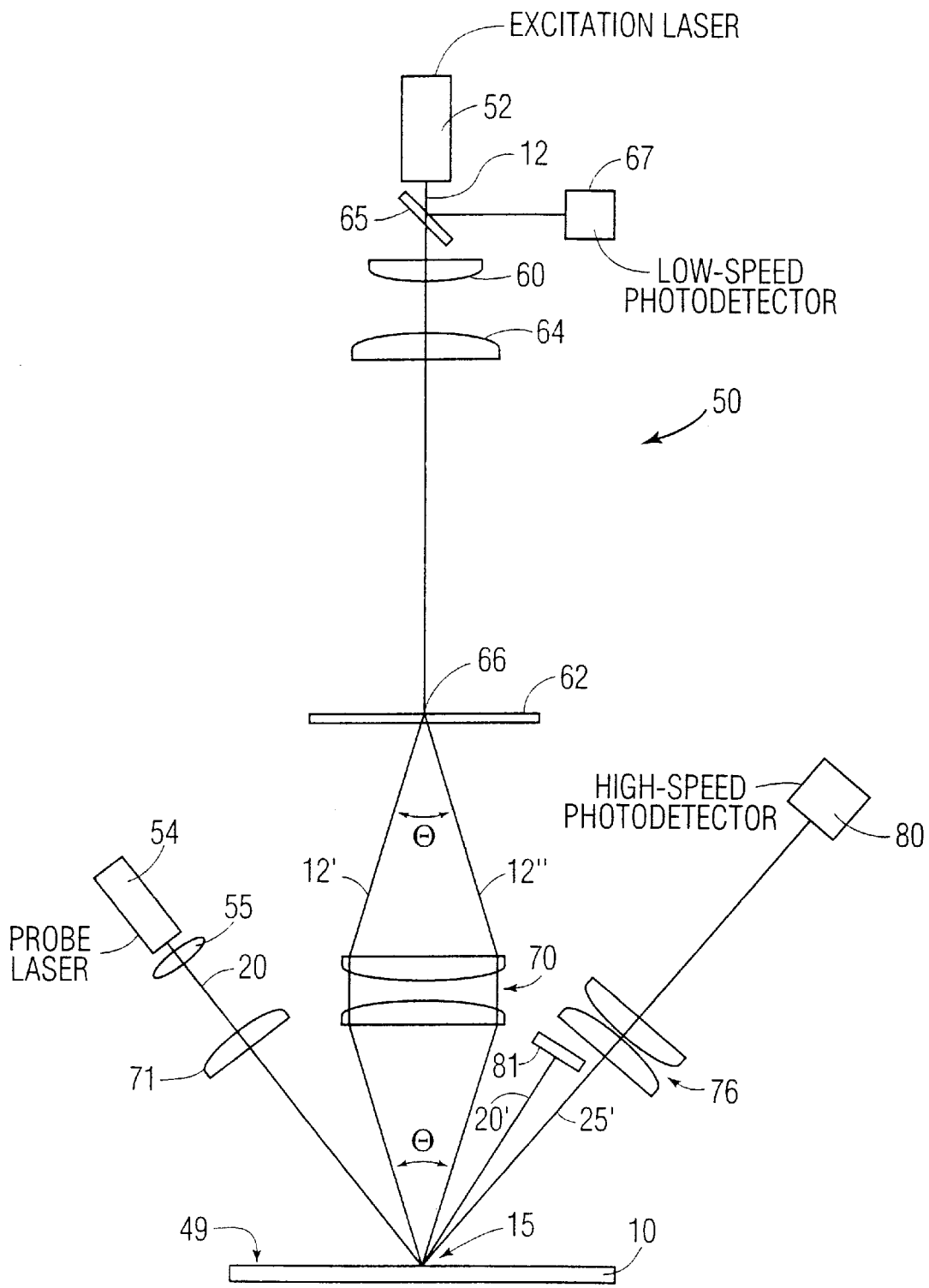
FIG. 7 is a schematic drawing of an optical system for measuring the concentration of ions implanted in a sample using ISS.

FIG. 7 shows an optical system 50 for measuring the properties of an ion-implanted sample 10 using ISS. A similar system suitable for making these measurements is described in SIMPLIFIED DEVICE AND METHOD FOR TIME-RESOLVED OPTICAL MEASUREMENTS (U.S. Ser. No. 08/377,310, filed Jan. 24, 1995), and IMPROVED METHOD AND APPARATUS FOR MEASURING MATERIAL PROPERTIES USING TRANSIENT GRATING SPECTROSCOPY (U.S. Ser. No. 08/885,555, filed concurrently herewith).

The system 50 includes an excitation laser 52 that initiates the acoustic and electronic responses, and a probe laser 54 that measures these responses. The optical properties of the excitation and probe lasers are described in reference to FIG. 1, above. The excitation laser, for example, can be a Nd:YAG laser or similar laser operating at a fundamental or harmonic wavelength. The probe laser can be a modulated diode laser. Both the excitation and probe lasers run at matched repetition rates that are typically in the range of 100–1000 Hz.

The excitation laser 52 generates a pulse 12 that is collimated with a first collimating lens 60 and then focused onto a phase mask 62 with a cylindrical lens 64. A portion of the pulse 12 is reflected by a glass cover slip 65 and detected with a low-speed photodetector 67 to generate an electrical pulse for triggering a data-acquisition system (not shown in the figure). The phase mask 62 includes a series of patterns 66, each of which generates a different grating pattern 15 on the sample 10. After impinging a pattern 66 on the phase mask 62, the excitation pulse 56 is diffracted into two sub-pulses 12', 12" which diverge at an angle θ determined by the pattern 66. Higher order diffracted beams are typically filtered out with a beam block (not shown in the figure). The diverging sub-pulses 12', 12" are collected with a first imaging lens pair 70 that focuses and overlaps them onto the surface 49 of the sample 10 to form the grating pattern 15. The first imaging lens 70 is positioned so that the grating pattern 15 has the same periodicity as the pattern 66 on the phase mask 62. Different grating patterns can be formed simply by translating the phase mask 62 so that a new pattern is irradiated with the incident excitation pulse 12.

The probe laser 54 generates a probe pulse 20 that is collimated with a second collimating lens 55 and focused on the grating pattern 15 with a second spherical lens 71 to measure the electronic and acoustic responses of the ion-implanted sample 10. As described above, the electronic or acoustic (or both) responses diffract a portion of the probe pulse 20 to form a signal beam 25. A beam-stop 81 blocks a reflected portion of the probe beam 20. A second imaging lens 76 collects the signal beam 74 and focuses it into a high-speed (e.g., 1 GHz) photodectector 80. This generates a light-induced electrical signal which is then analyzed with a computer (not shown in the figure) to determine the concentration of ions implanted in the sample.

The spatial dimensions of the excitation sub-pulses 12', 12" and probe pulse 20 focused onto the sample are chosen to maximize the amplitude of the signal waveform. The excitation sub-pulses are typically overlapped to form an elliptical grating pattern, with the long and short axes of the ellipse being between 150 and 25 microns, respectively. The distance between light and dark regions in the pattern is typically between 5 and 15 microns. The probe pulse is typically focussed to a spot that lies completely within the grating pattern. For example, the probe pulse can be focussed to a round spot with a diameter of less than 25 microns.

Ion-Implanted Materials

The above-describe method and apparatus can determine the concentration of ions implanted in different types of host samples. These samples include semiconducting materials, such as silicon-containing (e.g. polysilicon) films, silicon wafers, and films and wafers containing gallium arsenide, aluminum gallium arsenide, germanium, and derivatives and analogs thereof. Other samples that can be measured include ceramic materials, metals, and any other material that can be implanted with ions.

Implanted ions that can be measured include arsenic, argon, boron, oxygen, phosphorous, and any other ion which can alter the electrical properties of a host material.

Other Embodiments

Other embodiments are within the scope of the above-describe method and apparatus. For example, different optical systems, such as one including a different lens configurations as that described above, an amplitude mask in place of the phase mask, or a beamsplitter in place of the phase mask, can be used.

In another optical system, described in IMPROVED METHOD AND APPARATUS FOR MEASURING MATERIAL PROPERTIES USING TRANSIENT GRATING SPECTROSCOPY (U.S. Ser. No. 08/885,555, filed concurrently herewith), three sub-pulses, rather than two, are used to excite the sample through ISS. In this application, the three sub-pulses are equally spaced in a linear fashion (i.e., the center, right, and left beams) prior to being imaged onto the sample. When focused with a lens, the center beam propagates down a central optical axis of the beam-delivery system, while the right and left beams converge toward the same spot at the same angle but on opposite sides of the center beam. The beams are overlapped on the sample to form the transient grating that excites electronic or acoustic processes in the sample.

In general, any optical system for performing ISS or ISTS is suitable. Likewise, excitation and probe lasers that have suitable optical properties can be used in place of the lasers described above.

In other embodiments the signal waveform is processed by plotting it and then determining the area underneath the plot. This area is then compared to values in a database to determine the ion concentration. In other embodiments, the signal waveform is fit with a more complex function than that described above, such as a bi-exponential function that includes a relatively fast time constant and a relatively slow time constant. In this case, either the fast or slow time constant may be analyzed to determine the concentration of implanted ions. In still other embodiments, mathematical algorithms, such as algorithms based on kinetic modeling of a charge-carrier system, can be developed to relate the concentration of implanted ions to an amplitude or frequency contained in the signal waveform. Such algorithms would obviate the need for a database to determine the ion concentration.

Still other embodiments are within the scope of the following claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for determining a concentration of ions implanted in a material, comprising the steps of:
    passing an excitation pulse through a phase mask to generate at least two excitation laser sub-pulses;
    irradiating a region of the material with a grating pattern, formed by overlapping the at least two excitation laser sub-pulses, to initiate a time-dependent response in the region;
    diffracting a probe laser pulse, having a duration that is at least long as the time-dependent response, off the region to generate at least one time-dependent signal beam to generate a signal waveform;
    processing the signal waveform to determine the concentration of ions implanted in the material.

2. The method of claim 1, wherein the processing step includes the steps of:
    comparing the signal waveform to a mathematical function that represents the signal waveform; and
    determining an amplitude of the mathematical function to determine the amplitude of the signal waveform at a point in time.

3. The method of claim 2, wherein the mathematical function includes an exponential function.

4. The method of claim 3, wherein the exponential function is $S_0(t_0) [Ae^{-(t+t0)/\tau}]$ or a derivative thereof, wherein A is the amplitude, $\tau$ is a decay constant, t is time, and $S_0$ is a unit step function starting at $t=t_0$.

5. The method of claim 1, wherein the processing step further includes comparing the amplitude of the signal waveform to a database that correlates amplitudes of previously measured signal waveforms to concentrations of ions implanted in materials to determine the concentration of ions implanted in the material.

6. The method of claim 1, wherein the processing step further includes analyzing the amplitude with a mathematical algorithm to determine the concentration of ions implanted in the material.

7. The method of claim 1, wherein the processing step includes digitizing the signal waveform to generate a data set and then determining the amplitude of the signal waveform at a point in time by selecting a value from the data set.

8. The method of claim 1, wherein the processing step includes determining an area covered by a plot of the signal waveform.

9. The method of claim 8, wherein the processing step further includes comparing the area to a database that correlates the area with the concentration of ions implanted in a material to determine the concentration of ions implanted in the material.

10. The method of claim 1, wherein the probe laser beam comprises a laser pulse.

11. The method of claim 10, wherein the laser pulse has a duration that exceeds the duration of the time-dependent response.

12. The method of claim 1, wherein the material contains silicon.

13. The method of claim 12, wherein the material is a polysilicon film.

14. The method of claim 12, wherein the material is a silicon wafer.

15. The method of claim 1, wherein an ion implanted in the material is an ion of atoms selected from the group consisting of arsenic, argon, boron, and phosphorous atoms.

16. The method of claim 1, wherein the processing step further includes the steps of processing the signal waveform to determine a frequency, and analyzing the frequency to determine the concentration of ions implanted in the sample.

17. A method for determining a concentration of ions implanted in a silicon or polysilicon sample, comprising the steps of:
    generating at least two excitation laser sub-pulses;
    irradiating a region of the material with a grating pattern, formed by overlapping the at least two excitation laser sub-pulses, to initiate a time-dependent, decaying non-oscillatory response in the region;
    diffracting a probe laser pulse, having a duration that is at least long as the time-dependent response, off the region to generate a time-dependent signal beam;
    detecting the time-dependent signal beam to generate a signal waveform; and
    processing the signal waveform to determine the concentration of ions implanted in the silicon or polysilicon sample.

18. An apparatus for determining a concentration of ions implanted in a semiconducting material, comprising:
    an excitation laser for generating an excitation laser pulse;
    a beam-delivery system comprising a phase mask for separating the excitation laser pulse into at least two sub-pulses and then irradiating a region of the material with a grating pattern formed by overlapping the at least two sub-pulses to initiate a time-dependent response in the region;
    a probe laser for generating a probe laser pulse having a duration that is at least as long as the time-dependent response and an orientation such that the probe pulse diffracts off the region to generate a time-dependent signal beam;
    a photodetector for detecting the time-dependent signal beam to generate a signal waveform; and
    a processor for processing the signal waveform to determine the concentration of ions implanted in the material.

19. The apparatus of claim 18, wherein the processor is a computer that compares the signal waveform to a mathematical function and determines the amplitude of the signal waveform at a point in time by determining an amplitude of the mathematical function.

20. The apparatus of claim 18, wherein the processor is a computer that analyzes the amplitude of the signal waveform and compares the amplitude to a database to determine the concentration of ions implanted in the material.

21. The apparatus of claim 18, wherein the processor is a computer that determines the area covered by the signal waveform and compares the area to a database to determine the concentration of ions implanted in the material.

22. The method of claim 1, wherein the irradiation step further comprises initiating a time-dependent acoustic response and or a time-dependent electronic response, each of which has properties that depend on the concentration of ions implanted in the material.

23. The method of claim 1, wherein the diffracting step further comprises diffracting a probe pulse with a duration that is longer than both the electronic and acoustic responses.

24. The method of claim 17, wherein the processing step further includes comparing the amplitude of the signal waveform to a database that correlates amplitudes of previously measured signal waveforms to concentrations of ions implanted in materials to determine the concentration of ions implanted in the material.

25. The method of claim 17, wherein the processing step further includes analyzing the amplitude with a mathematical algorithm to determine the concentration of ions implanted in the material.

26. A method for determining a concentration of ions implanted in a material comprising:
- passing an excitation pulse through a phase mask to generate at least two excitation laser sub-pulses,
- irradiating a region of the material with a grating pattern, formed by overlapping two excitation laser sub-pulses, to initiate a time-dependent response in the region,
- diffracting a probe laser pulse, having a duration that is at least long as the time-dependent response, off the region to generate a time-dependent signal beam,
- detecting the time-dependent signal beam to generate a signal waveform,
- processing the signal waveform to determine its amplitude at a point in time, and
- comparing the amplitude of the signal waveform to a database that correlates amplitudes of previously measured signal waveforms to concentrations of ions implanted in materials to determine the concentration of ions implanted in the material.

* * * * *